United States Patent
Shigematsu et al.

(10) Patent No.: US 12,084,781 B2
(45) Date of Patent: Sep. 10, 2024

(54) HYDROGEN MIXED GAS GENERATION METHOD

(71) Applicant: FRIEND CO., LTD., Fukuoka (JP)

(72) Inventors: Isami Shigematsu, Fukuoka (JP); Naoki Hidaka, Fukuoka (JP)

(73) Assignee: FRIEND CO., LTD., Fukuoka (JP)

( * ) Notice: Subject to any disclaimer, the term of this patent is extended or adjusted under 35 U.S.C. 154(b) by 927 days.

(21) Appl. No.: 15/734,734

(22) PCT Filed: Jan. 9, 2019

(86) PCT No.: PCT/JP2019/000404
§ 371 (c)(1),
(2) Date: Dec. 3, 2020

(87) PCT Pub. No.: WO2019/234961
PCT Pub. Date: Dec. 12, 2019

(65) Prior Publication Data
US 2021/0230754 A1    Jul. 29, 2021

(30) Foreign Application Priority Data
Jun. 8, 2018    (WO) .................. PCT/JP2018/022068

(51) Int. Cl.
*C25B 1/042*    (2021.01)
*A61M 16/06*    (2006.01)
(Continued)

(52) U.S. Cl.
CPC ......... *C25B 1/042* (2021.01); *A61M 16/0666* (2013.01); *A61M 16/1095* (2014.02);
(Continued)

(58) Field of Classification Search
CPC ............. C25B 1/042; C25B 1/50; C25B 9/67; C25B 15/08; A61M 16/0666; A61M 16/1095;
(Continued)

(56) References Cited

U.S. PATENT DOCUMENTS

| | | | |
|---|---|---|---|
| 2009/0317671 | A1 | 12/2009 | Ukai et al. |
| 2011/0274615 | A1 | 11/2011 | Ishikawa |
| 2012/0039793 | A1 | 2/2012 | Takeshima |
| 2017/0022078 | A1 | 1/2017 | Fukuoka |

FOREIGN PATENT DOCUMENTS

| | | |
|---|---|---|
| CN | 101466635 A | 6/2009 |
| CN | 102369155 A | 3/2012 |

(Continued)

OTHER PUBLICATIONS

Machine translation of JP2017105692A (Year: 2017).*

*Primary Examiner* — Samir Shah
*Assistant Examiner* — Logan Edward Laclair
(74) *Attorney, Agent, or Firm* — ArentFox Schiff LLP; Michael Fainberg (57) ABSTRACT

A hydrogen mixed gas generation method using a device that includes a heating pipe housing therein a reduction acceleration member and a heating part including a heating device that heats the heating pipe includes a first process and a second process. The first process includes: causing raw water to flow into the heating pipe and heating the flowing raw water to generate water vapor; heating the generated water vapor to between 500° C. to 800° C.; causing the heated water vapor to be in contact with the reduction acceleration member that is heated along with the raw water to reduce the water vapor and generate hydrogen gas. The second process includes: diluting the hydrogen gas generated in the first process to obtain hydrogen mixed gas whose concentration of hydrogen gas is between 500 ppm to 20000 ppm.

6 Claims, 9 Drawing Sheets

(51) Int. Cl.
*A61M 16/10* (2006.01)
*A61M 16/12* (2006.01)
*C01B 3/10* (2006.01)
*C25B 1/50* (2021.01)
*C25B 9/67* (2021.01)
*C25B 15/08* (2006.01)

(52) U.S. Cl.
CPC ........ *A61M 16/122* (2014.02); *A61M 16/125* (2014.02); *C01B 3/10* (2013.01); *C25B 1/50* (2021.01); *C25B 9/67* (2021.01); *C25B 15/08* (2013.01); *A61M 2202/02* (2013.01); *C01B 2203/0855* (2013.01); *C01B 2203/1005* (2013.01); *Y02E 60/36* (2013.01)

(58) Field of Classification Search
CPC .............. A61M 16/122; A61M 16/125; A61M 2202/02; C01B 3/10; C01B 2203/0855; C01B 2203/1005; Y02E 60/36
See application file for complete search history.

(56) References Cited

FOREIGN PATENT DOCUMENTS

| | | |
|---|---|---|
| CN | 103140435 A1 | 6/2013 |
| CN | 106660841 A1 | 5/2017 |
| JP | 58-185685 A | 10/1983 |
| JP | 60-133088 A | 7/1985 |
| JP | 2006202509 A | 8/2006 |
| JP | 2006232593 A | 9/2006 |
| JP | 2007223843 A1 | 9/2007 |
| JP | 2013-151400 A | 8/2013 |
| JP | 2016-073583 A | 5/2016 |
| JP | 2017105692 A * | 6/2017 |
| RU | 2269486 C2 | 2/2006 |
| RU | 2440925 C1 | 1/2012 |
| RU | 2468263 C2 | 11/2012 |
| RU | 2509719 C1 | 3/2014 |
| RU | 2648263 C2 | 3/2018 |
| UZ | 3283 C | 12/2008 |
| WO | 2014024984 A | 2/2014 |
| WO | 2016/208163 A1 | 12/2016 |

* cited by examiner

HYDROGEN MIXED GAS GENERATION METHOD

CROSS-REFERENCE TO RELATED APPLICATION

This application is a national stage application of International Application No. PCT/JP2019/000404 filed on Jan. 9, 2019, which claims priority to PCT/JP2018/022068 filed on Jun. 8, 2018, the entire contents of which are herein incorporated by reference.

FIELD

Disclosed embodiments relate to a hydrogen mixed gas generation method.

BACKGROUND

It is conventionally known that it is effective to incorporate hydrogen into a human body in order to remove an active oxygen species that is considered as a cause that causes a lesion or dysfunction. Hence, a hydrogen mixed gas generation device is proposed that is capable of generating a hydrogen gas from a saturated vapor and incorporating a mixed gas that includes such a hydrogen gas into a human body (see, for example, Patent Literature 1).

CITATION LIST

Patent Literature

Patent Literature 1: Japanese Patent Application Publication No. 2013-151400

SUMMARY

However, hydrogen gas obtained by a conventional hydrogen mixed gas generating device is not yet proved to attain effective health promotion.

An aspect of embodiments is provided by taking the above into consideration and aims to provide a hydrogen mixed gas generation method that is capable of exerting higher effects on health promotion.

Solution to Problem (1) A hydrogen mixed gas generation method according to one aspect of embodiments using a device that includes a heating pipe housing therein a reduction acceleration member and a heating part including a heating device that heats the heating pipe includes a first process and a second process. The first process includes: causing raw water to flow into the heating pipe and heating the flowing raw water to generate water vapor; heating the generated water vapor to between 500° C. to 800° C.; causing the heated water vapor to be in contact with the reduction acceleration member that is heated along with the raw water to reduce the water vapor and generate hydrogen gas. The second process includes: diluting the hydrogen gas generated in the first process to obtain hydrogen mixed gas whose concentration of hydrogen gas is between 500 ppm to 20000 ppm.

(2) A hydrogen mixed gas generation method according to one aspect of embodiments, in accordance with the above-mentioned method (1), the heating part includes a coil heater that is wound around the heating pipe.

(3) A hydrogen mixed gas generation method according to one aspect of embodiments, in accordance with the above-mentioned method (1), the heating part includes an electromagnetic induction heating device.

(4) A hydrogen mixed gas generation method according to one aspect of embodiments, in accordance with any one of the above-mentioned methods (1) to (3), a concentration of the hydrogen gas in the hydrogen mixed gas obtained in the second process is between 1000 ppm to 3000 ppm.

(5) A hydrogen mixed gas generation method according to one aspect of embodiments, in accordance with any one of the above-mentioned methods (1) to (4), the reduction acceleration member includes: a first metal member that is formed of stainless and includes a cylindrical part where rod bodies respectively extend from both ends of the cylindrical part; and a plurality of second metal members that is formed of a steel material and is housed in the cylindrical part in a bundled state.

(6) A hydrogen mixed gas generation method according to one aspect of embodiments, in accordance with the above-mentioned method (5), lengths of the rod bodies respectively extending from the cylindrical part in the first metal member are set such that the cylindrical part is not in contact with the raw water.

DETAILED DESCRIPTION OF EMBODIMENTS

Hereinafter, embodiments of a hydrogen mixed gas generation method as disclosed in the present application will be explained in detail with reference to the accompanying drawings. Additionally, this invention is not limited by the embodiments as illustrated below.

Figure 1:
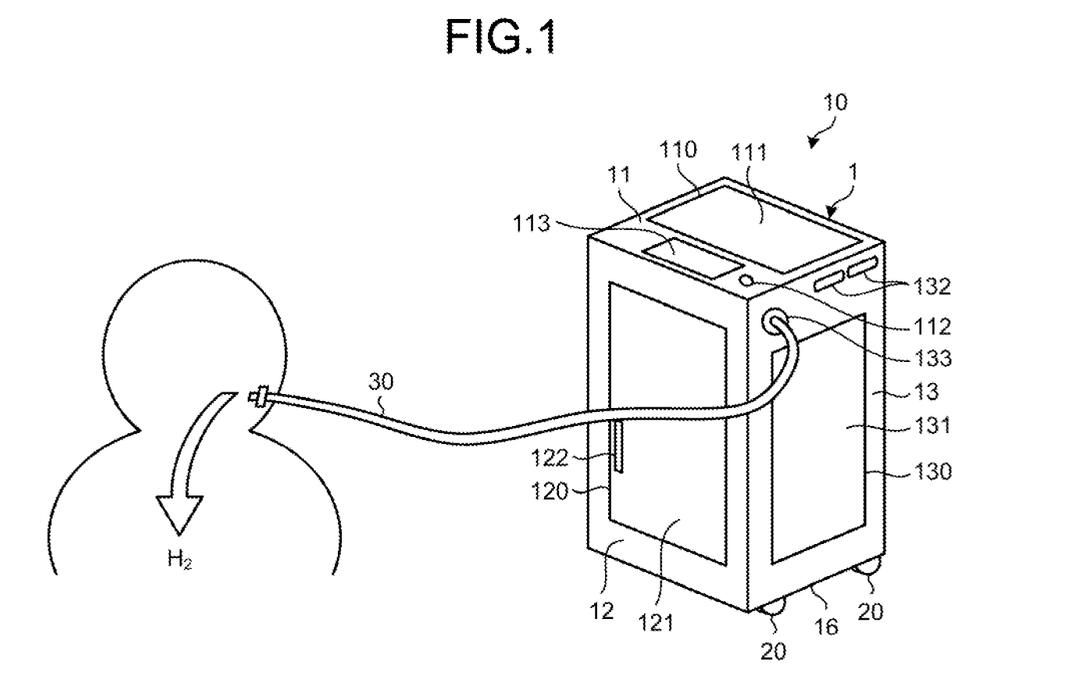
FIG. 1 is an explanatory diagram illustrating a state of use of a hydrogen mixed gas generation apparatus according to an embodiment.
Figure 2:
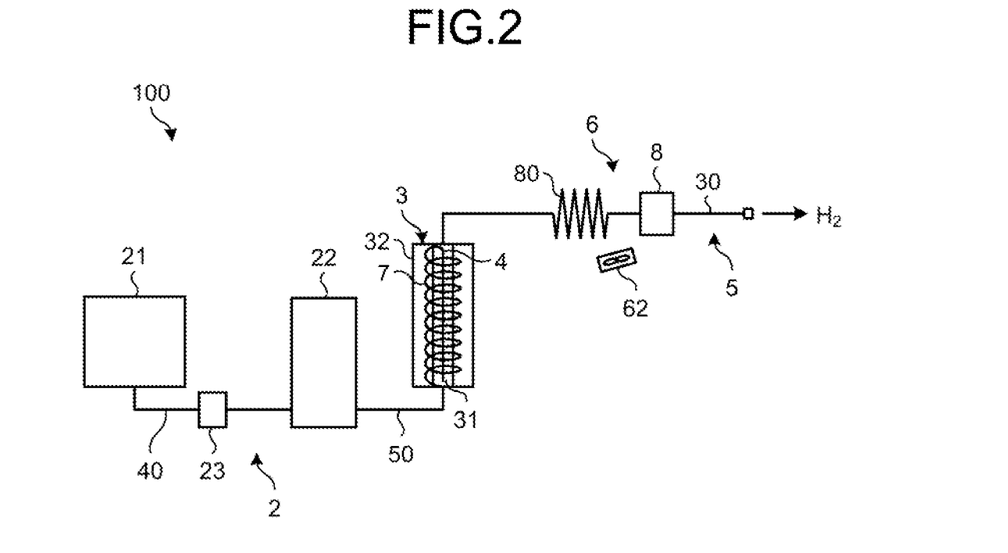
FIG. 2 is a schematic explanatory diagram illustrating one example of a hydrogen mixed gas generating unit according to the embodiment.

First, with reference to FIGS. 1 and 2, the outline of a configuration of a hydrogen mixed gas generation apparatus 10 for generating hydrogen mixed gas according to the present embodiment and a hydrogen mixed gas generation method executed by using the hydrogen mixed gas generation apparatus 10 will be explained. FIG. 1 is an explanatory diagram illustrating a state of use of the hydrogen mixed gas generation apparatus 10 according to an embodiment, and FIG. 2 is a schematic explanatory diagram illustrating one example of a hydrogen mixed gas generating unit according to the embodiment.

The hydrogen mixed gas generation apparatus 10 according to the present embodiment is configured to generate mixed gas including vapor and hydrogen gas ($H_2$), and adjust a hydrogen concentration to appropriate one for incorporation into a human body. As illustrated in FIG. 1, a user wears a tip of a gas inhalation tube 30 that extends from a casing 1 at his/her nose, so that it is possible to aspirate a produced hydrogen gas from a nasal cavity. In the present embodiment, the number of users is one; however, a plurality of connection parts 133 may be provided to the gas inhalation tube 30, or a plurality of branches may be provided to the gas inhalation tube 30 to be used by two or more users. Note that, for example, a cannula or the like may be preferably employed for the gas inhalation tube 30.

As illustrated in FIG. 1, the casing 1 of the hydrogen mixed gas generation apparatus 10 is formed into a rectangular box shape by a bottom wall 16, a ceiling wall 11, and four peripheral walls 12, 13, 14, 15 (see FIG. 4), and casters 20 with a spherical shape are attached to four corners of the bottom wall 16.

The casing 1 is formed of a stainless or steel plate having an appropriate thickness. As illustrated in FIG. 1, a top access port 110 is formed on the ceiling wall 11 that occupies a majority of an area of the ceiling wall 11, and such the top access port 110 is covered by a lid body 111 that is provided to be attachable thereto and detachable therefrom. A power source switch 112 and a touch panel 113 that functions as an operation part are provided on a front side of the lid part 111.

A front access port 120 that occupies a majority of an area of the front wall 12 is formed on the front wall 12 that is one of peripheral walls of the casing 1. A front door 121 including a handle 122 is attached to the front access port 120 via a not-illustrated hinge to be re-closable.

Moreover, also on the left wall 13 that is one of peripheral walls of the casing 1, a side access port 130 is formed that occupies a majority of an area of the left wall 13 and the side access port 130 is covered by a lid body 131 so as to be attachable thereto and detachable therefrom. Additionally, in the hydrogen mixed gas generation apparatus 10 according to the present embodiment, it is possible to execute maintenance on a control unit 101 (see FIGS. 3 and 4) as described later from the side access port 130. A plurality of ventilation holes 132 and 132 are formed above the side access port 130 and at positions near an upper edge part. The connection part 133 of the gas inhalation tube 30 is arranged at a front position of the ventilation holes 132 and 132.

Additionally, the plurality of ventilation holes 132 and 132 are also formed at positions near upper edge parts of the right wall 14 and the back wall 15 that are constituting the peripheral walls of the casing 1.

A hydrogen mixed gas generation unit 100 is housed in the casing 1. As illustrated in FIG. 2, the hydrogen mixed gas generation unit 100 includes a water supply part 2, a vapor heating part 3, a gas extraction part 5, and a cooling part 6. In a first process, the vapor heating part 3 heats raw water supplied from the water supply part 2 so as to generate vapor, further heats the heated vapor to between 500° C. to 800° C., more preferably between 650° C. to 750° C., and generates high temperature vapor mixed gas containing hydrogen gas. Next, as a second process, hydrogen gas generated in the first process is mixed with secondary air taken into the system and is cooled down, and further is diluted to a concentration of 1000 ppm to 3000 ppm (0.1 Vol % to 0.3 Vol %) to be able to obtain hydrogen mixed gas whose temperature is appropriate for incorporation into a human body.

Figure 3:
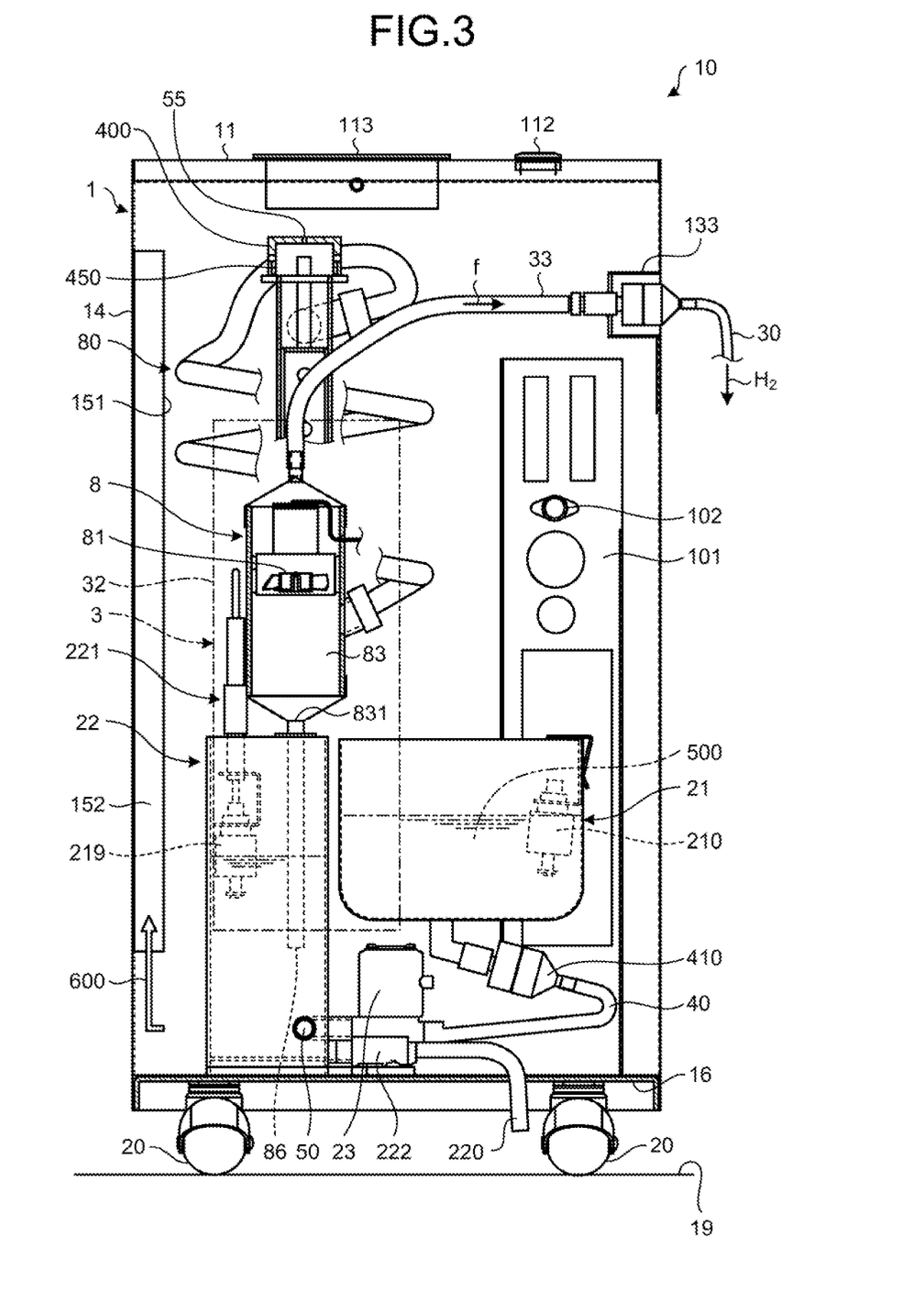
FIG. 3 is an explanatory diagram illustrating one example of a configuration of the hydrogen mixed gas generation apparatus according to the embodiment in a front view thereof.
Figure 4:
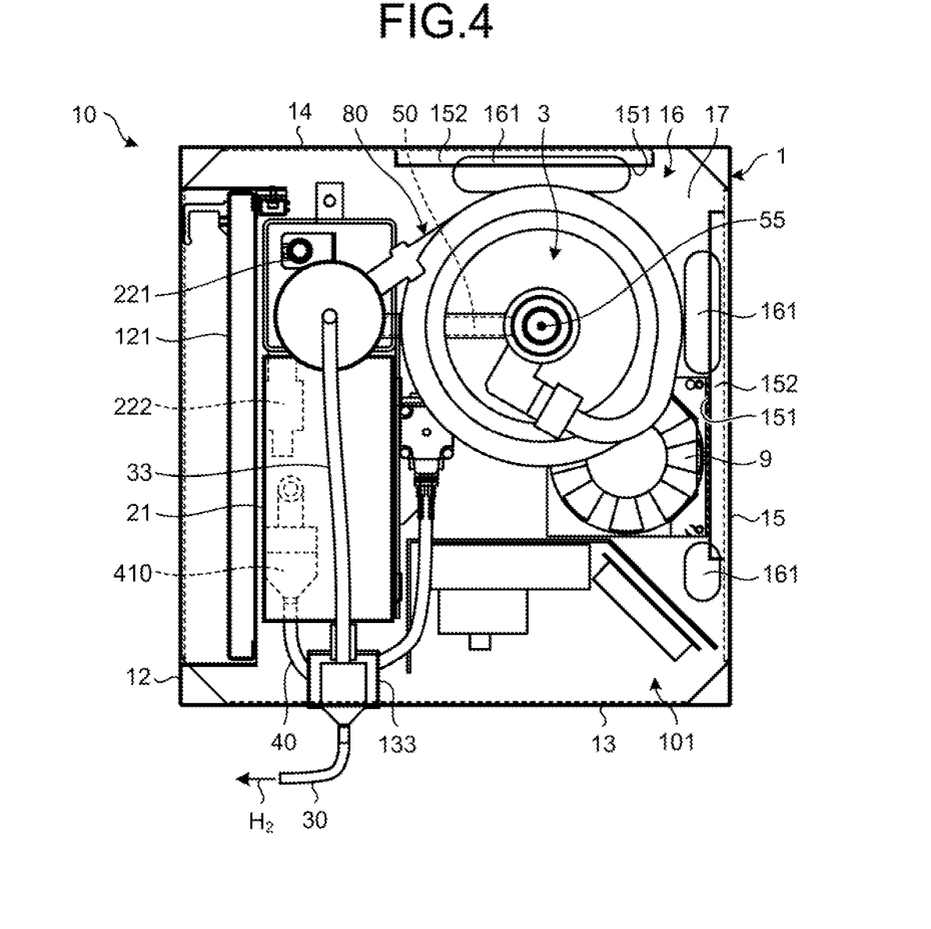
FIG. 4 is an explanatory diagram illustrating one example of a configuration of the hydrogen mixed gas generation apparatus according to the embodiment in a plan view thereof.
Figure 5:
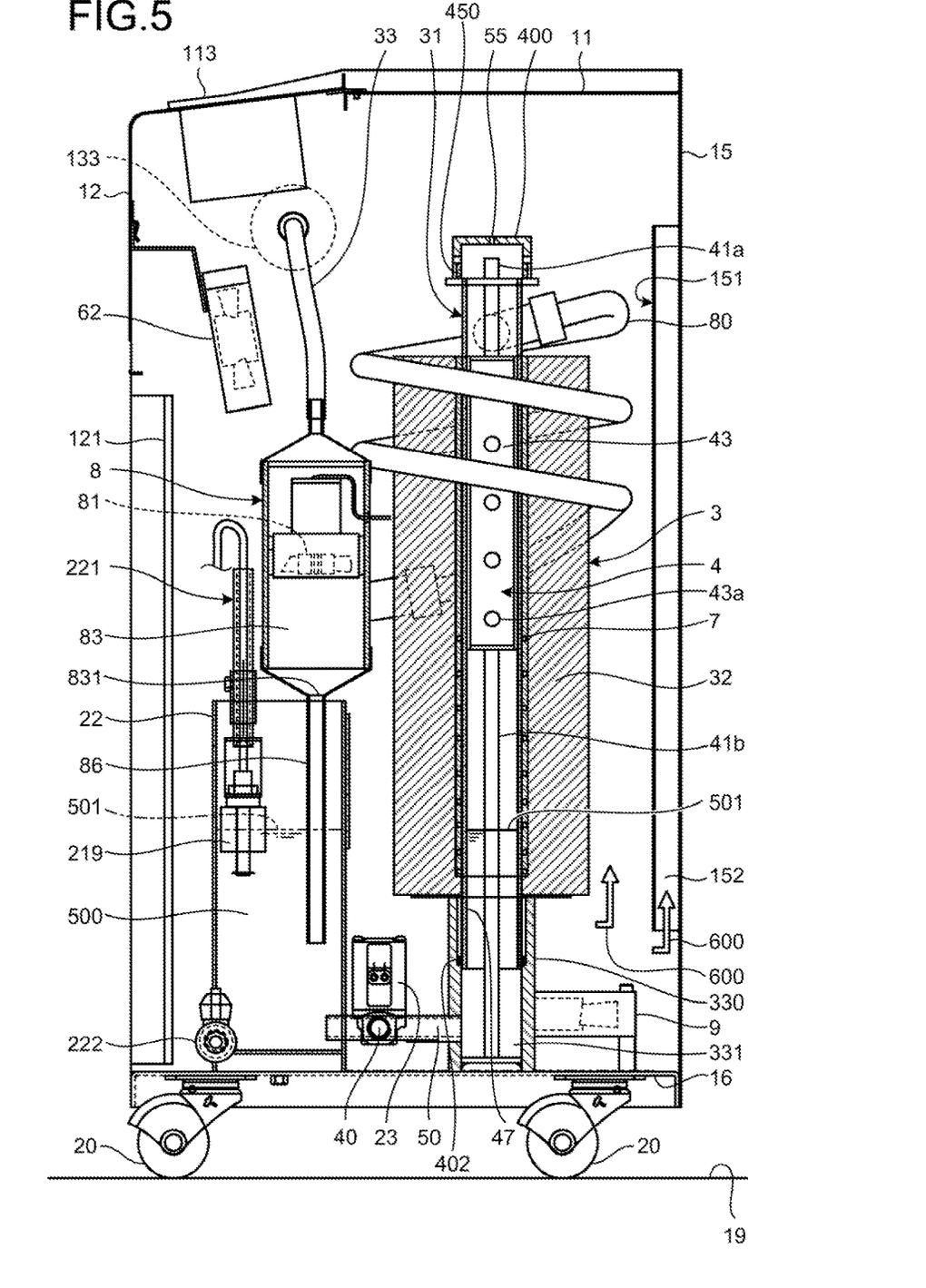
FIG. 5 is an explanatory diagram illustrating one example of a configuration of the hydrogen mixed gas generation apparatus according to the embodiment in a side view thereof.
Figure 6:
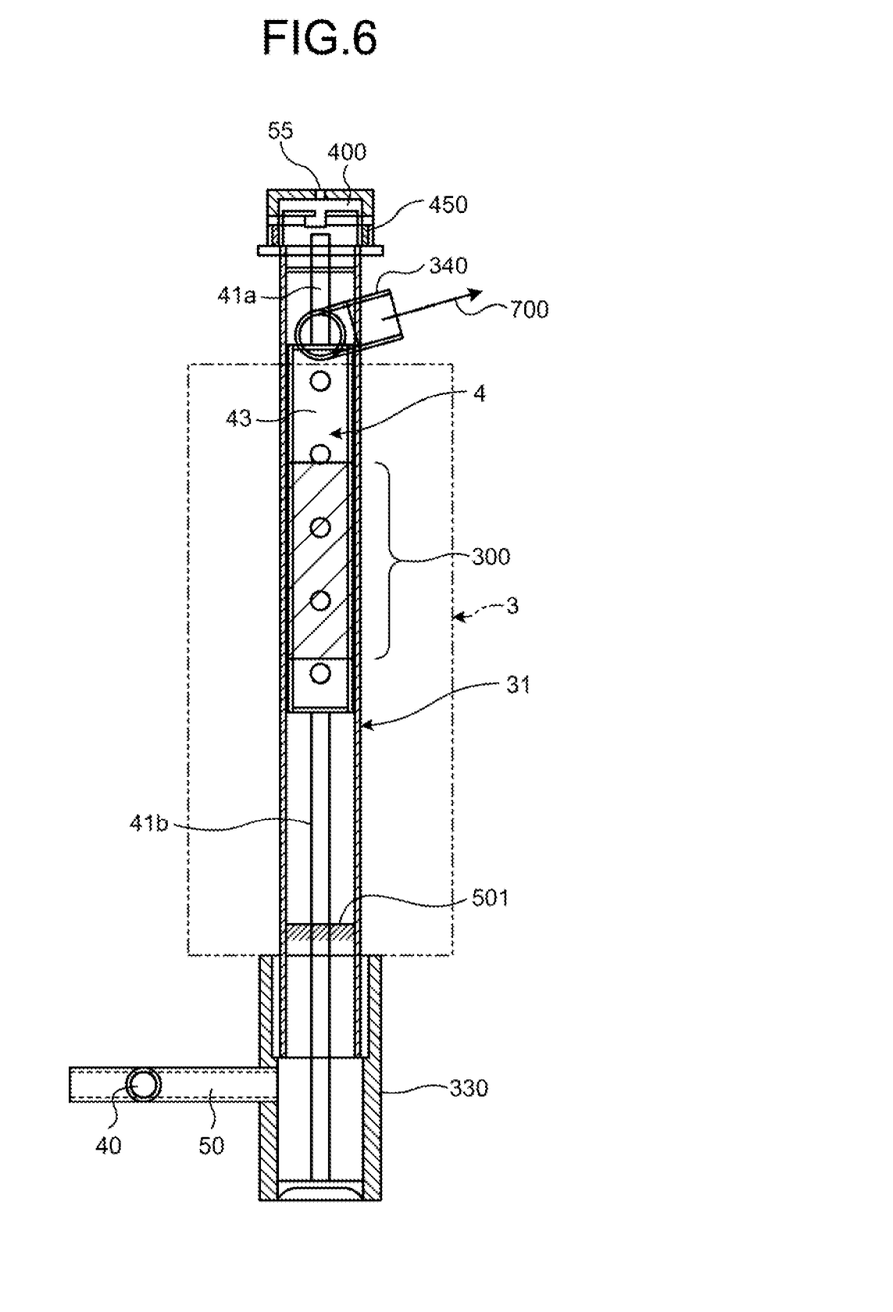
FIG. 6 is a front view illustrating a heating pipe that includes an air intake part according to the embodiment.

FIG. 3 is an explanatory diagram illustrating one example of a configuration of the hydrogen mixed gas generation apparatus 10 according to the embodiment in a front view thereof, FIG. 4 is an explanatory diagram illustrating one example of a configuration of the above-mentioned hydrogen mixed gas generation apparatus 10 in a plan view thereof, and FIG. 5 is an explanatory diagram illustrating one example of a configuration of the above-mentioned hydrogen mixed gas generation apparatus 10 in a side view thereof. FIG. 6 is a front view illustrating a heating pipe that includes an air intake part according to the embodiment. Additionally, in FIGS. 3 and 5, a reference symbol 19 indicates a floor surface that is a placement surface for the hydrogen mixed gas generation apparatus 10. Furthermore, in all of the drawings in addition to FIG. 2, appropriate simplification is applied to facilitate understanding.

Details of the hydrogen mixed gas generation unit 100 will be specifically explained. As illustrated in FIGS. 2 to 5, the water supply part 2 includes a water supply tank 21 that stores therein raw water 500 and an adjustment tank 22 that adjusts a liquid level of the raw water 500 to be supplied to the vapor heating part 3. As illustrated in FIGS. 3 and 5, a level switch 210 that detects an amount of water of the raw water 500 is arranged in the water supply tank 21, and a water supply level meter 221 is arranged in the adjustment tank 22.

A water drainage hose 220 is attached to the adjustment tank 22 through a water drainage valve 222 to be able to drain water in the adjustment tank 22. The water supply tank 21 and the adjustment tank 22 are communicated with each other by a water supply pipe 40 through an electromagnetic valve 23. An opening or closing operation of the electromagnetic valve 23 is controlled by the control unit 101 (see FIG. 4) in accordance with a value of the water supply level meter 221. Additionally, in FIGS. 3 and 4, a reference symbol 410 indicates a coupler of the water supply pipe 40. In FIGS. 3 and 5, a reference symbol 219 indicates a float provided in the water supply level meter 221.

The vapor heating part 3 includes a heating pipe 31 into which the raw water 500 flows from the adjustment tank 22 and a heating device. Herein, as the heating device, there is provided a coil heater 7 that is wound around a periphery of the heating pipe 31 over a substantially total length thereof. In other words, the vapor heating part 3 heats the raw water 500, which is supplied from the water supply part 2 to the heating pipe 31 via a communication pipe 50, by using the coil heater 7 so as to generate vapor, and further heats the vapor to between 650° C. to 750° C. A periphery of the coil heater 7 is covered by a heat insulation material 32 having a predetermined thickness.

An amount of the raw water 500 to be supplied to the heating pipe 31 is maintained constant by the adjustment tank 22. That is, as illustrated in FIG. 5, a liquid level 501 in the adjustment tank 22 and the liquid level 501 in the heating pipe 31 are identical levels.

As illustrated in FIG. 5, the heating pipe 31 into which the raw water 500 flows is attached, via a heat insulation sleeve 47, to an upper end part of a cylindrical body 330 with which the communication pipe 50 communicated with the water supply part 2 is connected. In the heating pipe 31, there is housed a reduction acceleration member 4 (see FIG. 6) for accelerating generation of hydrogen gas. The reduction acceleration member 4 is formed of stainless so as to include a first metal member including a cylindrical part 43 where rod bodies respectively extend from both ends thereof, and a plurality of second metal members that are formed of a steel material and housed in the cylindrical part 43 in a bundled state. In FIG. 5, a space indicated by a reference symbol 331 is a water reservoir that is formed in the cylindrical body 330 connected with the heating pipe 31.

By employing the reduction acceleration member 4, in the hydrogen mixed gas generation apparatus 10 according to the present embodiment, heated vapor is efficiently reduced so as to improve generation efficiency of hydrogen gas, so that it is possible to stably generate hydrogen gas whose amount meets the needs. Details of the reduction acceleration member 4 will be mentioned later.

As illustrated in FIG. 6, a part upper than the liquid level 501 in the heating pipe 31 is a superheated region 300 in which the generated vapor is heated to between 650° C. to 750° C., and is turned into superheated vapor. In other words, in an inner part of the heating pipe 31, there presents hydrogen mixed gas in which hydrogen gas and superheated vapor are mixed in a high temperature state. The hydrogen mixed gas is delivered to a heat radiation tube 80 from an exhaust cylinder 340 arranged at an upper part of the heating pipe 31 (arrow 700). Note that a concentration of hydrogen gas generated in the process is 4.2% (42000 ppm). In order to keep a concentration of hydrogen gas within a range between 1000 ppm to 3000 ppm in the next process, it is desirable that a concentration of hydrogen gas in this process is equal to or less than 4.2%.

Incidentally, in the heating pipe 31 according to the present embodiment, an inside diameter thereof is approximately 30 mm and a total length thereof is 345 mm, and the superheated region 300 formed therein has approximately between 60 mm to 80 mm. A total length of the heating pipe 31 may be set to between 100 mm to 700 mm in accordance with a size of the casing 1, in this case, a range of the superheated region 300 is approximately between 20 mm to 430 mm.

By employing the superheated region 300, it is possible to adjust a temperature into appropriate one for inhalation by mixing with secondary air to be mentioned later, and it is further possible to obtain, even under ordinary pressure, vapor mixed gas in which a concentration of hydrogen gas ($H_2$) is diluted to between 1000 ppm to 3000 ppm (approximately 0.1% to 0.3%), which is appropriate for incorporation into a human body.

As illustrated in FIGS. 2 to 5, the gas extraction part 5 includes the heat radiation tube 80, a gas delivery case 8, and the gas inhalation tube 30. That is, the gas delivery case 8 is connected to another end of the heat radiation tube 80 with one end that is communicated with a top of the heating pipe 31 and the gas inhalation tube 30 is communicated with the gas delivery case 8 through a leading tube 33.

As illustrated in FIGS. 3 to 5, at an upper end part of the heating pipe 31 into which the raw water 500 flows, there is arranged a gas intake part 55 for taking secondary air into high-temperature hydrogen mixed gas in which hydrogen gas and superheated vapor are mixed to each other. In other words, a cap body 400 is provided to an upper end of the heating pipe 31, via a sealing material 450, to be attachable thereto and detachable therefrom, a pinhole formed in the cap body 400 is used as the gas intake part 55.

A diameter of the pinhole is decided by an amount of secondary air to be taken into the system for keeping a concentration of hydrogen gas within a range between 1000 ppm to 3000 ppm. It is found that in the above-mentioned heating pipe 31 of the hydrogen mixed gas generation apparatus 10 according to the present embodiment, a concentration of hydrogen gas generated by an oxidation-reduction reaction between water vapor heated to between 650° C. to 750° C. and the reduction acceleration member 4 is 42000 ppm, and in order to keep the concentration of the hydrogen gas within a range between 1000 ppm to 3000 ppm, a required amount of the secondary air flowing into the system is between 0.2 L/min to 1.0 L/min. In order to realize the above-mentioned, a diameter of the pinhole is to be less than 5 mm. Particularly, it is preferable that the diameter of the pinhole is set to approximately 1.0 mm to 2.0 mm.

In the present embodiment, a required amount of secondary air is set to between 0.4 L/min to 0.5 L/min, and thus a diameter of the pinhole is set to 1.2 mm in accordance therewith. Note that in the hydrogen mixed gas generation apparatus 10 according to the present embodiment, an amount of secondary air flowing into the system is approximately 0.4 L/min from actual measurement.

As illustrated in FIGS. 3 and 5, by employing the gas intake part 55, outside air is taken into the heating pipe 31 by operation of a gas supply fan 81 provided in the gas delivery case 8, and is further delivered to the gas delivery case 8 along with vapor mixed gas via the heat radiation tube 80 to be delivered to the gas inhalation tube 30.

Thus, an appropriate amount of fresh outside air is taken, as secondary air, into vapor mixed gas containing hydrogen gas and the hydrogen mixed gas is diluted into a concentration within a range between 1000 ppm to 3000 ppm, and further it is possible to cool down the vapor mixed gas to a temperature that is appropriate for incorporation into a human body.

As described above, caused by the gas supply fan 81, hydrogen mixed gas having an appropriate concentration that is delivered to a primary side of the gas supply fan 81 in the gas delivery case 8 is further delivered (see arrow f illustrated in FIG. 3) to the gas inhalation tube 30 via the leading tube 33 that is communicated with a secondary side of the gas supply fan 81. The hydrogen mixed gas, which is sufficiently cooled down in the above-mentioned travel, is smoothly delivered to the outside of the system from the gas inhalation tube 30 (cannula), and is further delivered to a nasal cavity of a user from the gas inhalation tube 30 (cannula) to be incorporated into a human body via a mucous membrane of the nasal cavity.

Meanwhile, as illustrated in FIGS. 2 to 5, the heat radiation tube 80 that composes a part of the gas extraction part 5 is configured to be a coil shape and thereby facilitate heat radiation, and composes a part of the cooling part 6. Therefore, it is also possible to consider that the cooling part 6 is included in the gas extraction part 5. The cooling part 6 includes the heat radiation tube 80 and a cooling fan 62 (see FIG. 5) that is arranged and provided in such a manner that it is possible to blow wind toward the heat radiation tube 80.

As illustrated in FIGS. 3 to 5, the heat radiation tube 80 that is formed into a coil shape is arranged and provided so as to surround a periphery of the heat insulation material 32 of the vapor heating part 3. By employing such a configuration, it is possible to effectively utilize an internal space of the casing 1 to be able to prevent needless upsizing of the casing 1, so that it is possible to facilitate miniaturization of the hydrogen mixed gas generation apparatus 10.

The gas intake part 55 is arranged at an upper end of the heating pipe 31. Thus, the gas intake part 55 is positioned at an upper part of an inner part of the casing 1 and there presents no obstacle or the like around the gas intake part 55, so that maintenance work is easy.

A position at which the gas intake part 55 is arranged is not limited to an upper end of the heating pipe 31. The position may be anywhere as long as the position is on an upper flow side of the gas supply fan 81 and on a flow path through which vapor mixed gas generated by the vapor heating part 3 is aspirated.

The gas intake part 55 may be provided with a filter, so that impurities and the like are removed from the aspirated air so as to dilute the hydrogen gas by using clean air.

Incidentally, as illustrated in FIGS. 3 and 5, a water droplet discharge port 831 is formed on a bottom part of the gas delivery case 8 so as to be communicated with a gas convection space 83 that is formed on a primary side of the gas supply fan 81. A proximal end of a drain pipe 86 is connected with the water droplet discharge port 831 and a distal end of the drain pipe 86 faces an inside of the adjustment tank 22. Thus, in the gas delivery case 8, while the mixed gas is gas-supplied smoothly, a vapor that is not completely vapor-liquid-separated is retained in the gas convection space 83 and simultaneously is condensed therein and condensed water is returned to the adjustment tank 22.

As illustrated in FIG. 5, the cooling fan 62 is arranged and provided so as to be tilted by a predetermined angle, so that it is possible to blow wind in such a manner that the wind is blown in a direction that traverses the heat radiation tube 80 obliquely upward. Therefore, it is possible to apply wind to the heat radiation tube 80 efficiently and yet it is possible to discharge warm air that strips heat from the heat radiation tube 80 from the ventilation hole 132 that is formed on a side wall of the casing 1 to an outside of the casing 1.

Next, with reference to FIGS. 6 to 8B, the reduction acceleration member 4 housed in the heating pipe 31 constituting the vapor heating part 3 will be specifically explained. FIG. 6 is a front view illustrating the heating pipe 31 that includes the gas intake part 55 according to the embodiment. FIG. 7A is a front view illustrating the reduction acceleration member 4 according to the embodiment, and FIG. 7B is a plan view illustrating the above-mentioned reduction acceleration member 4. FIG. 8A is an enlarged cross-sectional view along line A-A in FIG. 7A.

The reduction acceleration member 4 that is housed in the heating pipe 31 into which the raw water 500 is flowing is composed of, for example, a metal that is readily oxidized, such as iron, in other words, a metal that is readily rusted. The reduction acceleration member 4 may be made of a metal that is readily changes to a cation such as Li, K, Ca, Na, Mg, Al, Zn, Fe, Ni, Sn, Pb, Cu, and Hg, in other words, a metal that is readily oxidized. In the present embodiment, iron (Fe) is employed for the reduction acceleration member 4.

Figure 7A:
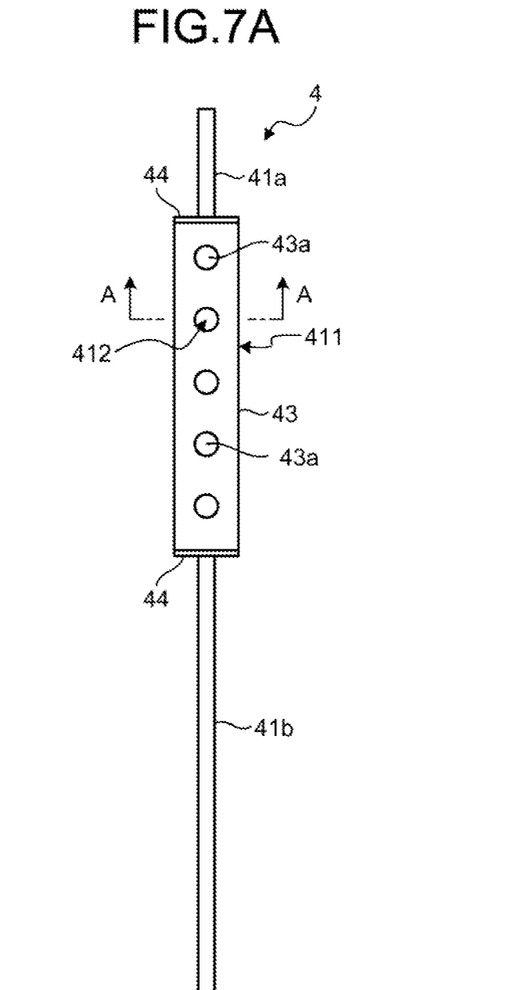
FIG. 7A is a front view illustrating a reduction acceleration member according to the embodiment.
Figure 7B:
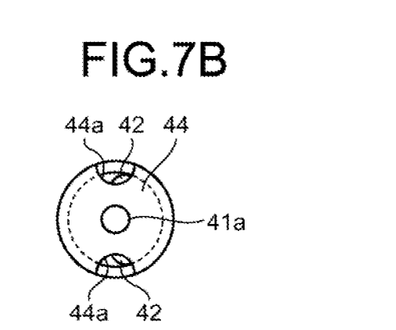
FIG. 7B is a plan view illustrating the reduction acceleration member according to the embodiment.
Figure 8A:
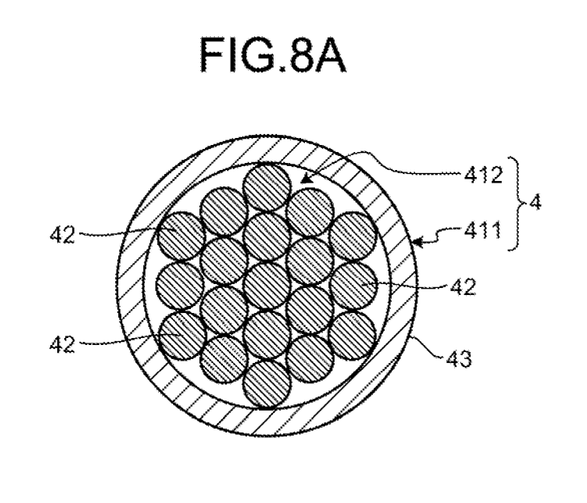
FIG. 8A is an enlarged cross-sectional view along line A-A in FIG. 7A.

In other words, as illustrated in FIG. 7A, the reduction acceleration member 4 according to the present embodiment includes a holding member 411 that is the first metal member, for example, that is formed of a stainless steel and has a cylindrical part 43 where rod bodies respectively extend from both ends thereof, and an iron rod member 412 that is the second metal member, for example, where a plurality of steel materials 42 with a rod shape is bundled. In the present embodiment, as illustrated in FIG. 8A, the iron rod member 412 is housed in the cylindrical part 43 of the holding member 411 in a dense state. The iron rod member 412 substantially serves a function of reduction acceleration, where, in the present embodiment, a diameter of the steel material 42 that is a so-called round steel with a circular shape in a cross-section thereof is 4 mm and S45C is used for material thereof.

Thus, the steel materials 42 that are round steels are densely bundled with no space, so that it is possible to transfer heat to an inside of the cylindrical part 43 efficiently. Therefore, heat efficiently transfers to a whole of the iron rod member 412, so that it is possible to accelerate an oxidation-reduction reaction with vapor.

Additionally, as described above, the reduction acceleration member 4 is formed in a cartridge including the holding member 411 and the iron rod member 412, and thus maintenance work such as replacement is easy.

Meanwhile, as illustrated in FIG. 7A, the cylindrical part 43 of the holding member 411 is provided with a structure in such a manner that openings of a cylindrical body on both ends thereof are blocked by cap materials 44. Then, a plurality of hole parts 43a is formed on a peripheral surface of a cylindrical body and a pair of communication holes 44a with a semicircular shape is oppositely formed on the cap materials 44, in such a manner that it is possible for vapor in the heating pipe 31 to be sufficiently in contact with the iron rod member 412 that is housed in an inside thereof. Vapor penetrates from the hole parts 43a into an inside of the cylindrical part 43 so as to cause an oxidation-reduction reaction with the iron rod member 412.

Among two rod bodies that are included by the cylindrical part 43, a length of a first rod body 41a with an end that is connected to the cap material 44 that is provided on an upper end part of a cylindrical body in FIG. 7A is different from that of a second rod body 41b with an end that is connected to the cap material 44 that is provided on a lower end part of the cylindrical body. That is, as illustrated in FIG. 6, the second rod body 41b is formed to be relatively long, so that the iron rod member 412 in the cylindrical part 43 is never dipped in the raw water 500 and is located in the superheated region 300 arranged upper than the liquid level 501 in the heating pipe 31.

Therefore, the raw water 500 that is supplied to the heating pipe 31 is heated by the coil heater 7 to be changed into vapor, and superheated vapor further heated by the coil heater 7 is efficiently in contact with the iron rod member 412 of the reduction acceleration member 4 whose reduction reaction is accelerated by heating of the coil heater 7 so as to generate hydrogen mixed gas containing hydrogen gas.

As illustrated in FIGS. 5 and 6, at least the second rod body 41b of the holding member 411 is dipped in the raw water 500. Hence, all materials of the holding member 411 including the second rod body 41b are stainless steel such as SUS 304. In a case where stainless steel is used, even when the holding member 411 is dipped in water, it is possible to prevent red rust that redly clouds the raw water 500 and further degrades appearance.

The iron rod member 412 that is housed in the cylindrical part 43 of the holding member 411 is exposed to superheated vapor in the heating pipe 31 at a high temperature, so that an active oxidation-reduction reaction is caused so as to strip oxygen and reduce the superheated vapor, and the iron rod member 412 reacts with oxygen to be oxidized. Thus, such an oxidation-reduction reaction is caused in the heating pipe 31, so that generation of hydrogen gas is accelerated. Additionally, in association with such an action, black rust is generated on a surface of the iron rod member 412 as time passes.

Figure 8B:
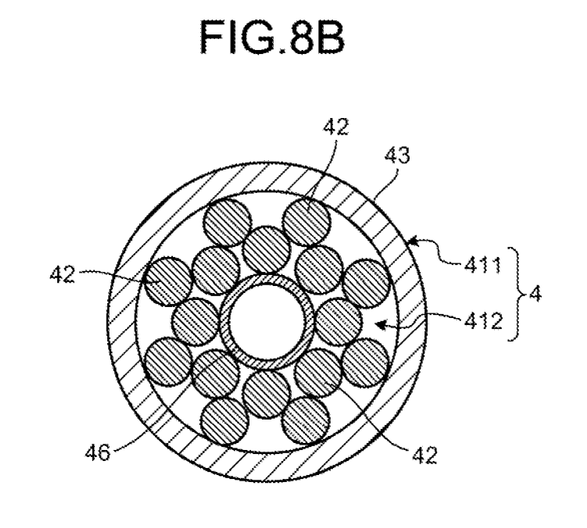
FIG. 8B is an explanatory diagram illustrating the reduction acceleration member according to the modification in a cross-sectional view thereof.

Incidentally, it is also possible to provide the reduction acceleration member 4 with a configuration as illustrated in FIG. 8B. FIG. 8B is an explanatory diagram illustrating the reduction acceleration member 4 according to a modification in a cross-sectional view thereof. As illustrated in FIG. 8B, the reduction acceleration member 4 according to the modification is configured in such a manner that the plurality of steel materials 42 that is rod-shaped members is bundled and a pipe member 46 that is readily thermally-deformed is arranged at a central position thereof. That is, in the iron rod member 412 that is housed in the cylindrical part 43 of the holding member 411, the pipe member 46 with a material that is S45C similarly to the steel materials 42 is arranged at the center thereof and the plurality of steel materials 42 that is rod-shaped members is bundled around the pipe member 46. Herein, it is preferable for a diameter of the pipe member 46 to be greater than a diameter of the steel material 42 that is 4 mm. Herein, a diameter of the pipe member 46 is set to 8 mm.

This is, for example, like the configuration as illustrated in FIG. 8A, where, as the steel materials 42 are densely bundled with no space and are housed in the cylindrical part 43, deformation of each of the steel materials 42 is caused by thermal expansion thereof. Hence, the pipe member 46 with a large diameter that is deformed more readily although an identical material is applied thereto is arranged at a central part of the iron rod member 412. By such a configuration, the pipe member 46 absorbs an expansion force that is going to deform the steel materials 42, so that it is possible to prevent deformation of the iron rod member 412.

Additionally, a size of the iron rod member 412 such as a diameter and a length thereof is not limited to one that has been exemplified in the present embodiment, and it is possible to appropriately and comprehensively determine the size while taking into consideration a desired generation amount of hydrogen mixed gas, an amount of heating, and the like.

The above-mentioned reduction acceleration member 4 is provided to be insertable into and removable from an upper end of the heating pipe 31. Hence, it is possible for anyone to simply set the reduction acceleration member 4 by merely executing insertion thereof through an opening of the heating pipe 31 at an upper end thereof. After the reduction acceleration member 4 is housed in the heating pipe 31, it is preferable to close a lid for an opening of the heating pipe 31 at an upper end thereof. On the other hand, in a case where the reduction acceleration member 4 or the like is extracted from the heating pipe 31 in order to execute replacement thereof, it is possible to open a lid and pinch and simply extract the first rod body 41a of the holding member 411. Note that, in FIG. 5, a reference symbol 402 indicates a sealing member such as packing.

As described above, the reduction acceleration member 4 according to the present embodiment has been explained; however, needless to say, a configuration of the reduction acceleration member 4 is not strictly limited to the above-mentioned mode. For example, an unevenness portion (not illustrated) may be formed on a surface of each of the steel materials 42 constituting the second metal members so as to increase its surface area. A shape of the steel material 42 has been set to be rod-shaped in consideration of efficiency of heat conduction; however, not limited to a solid rod body, may be hollow pipe-shaped. Furthermore, the steel material 42 may be sphere-shaped instead of one that is rod-shaped.

In the above-mentioned configuration, as illustrated in FIG. 4, the vapor heating part 3 of the hydrogen mixed gas generation apparatus 10 according to the present embodiment is arranged closely to a corner part 17 formed of the right wall 14 that is a first side wall and the back wall 15 that is a second side wall of the casing 1. In other words, the coil heater 7 is covered with the heat insulation material 32, on the other hand, the vapor heating part 3 that becomes a high temperature is arranged in a neighborhood of the corner part 17 formed of the right wall 14 and the back wall 15. Thus, for example, the control unit 101 (see FIG. 3) is able to be arranged in a neighborhood of the left wall 13, and thus the control unit 101 is able to be arranged away from the vapor heating part 3 so as to prevent effects due to the heat. Moreover, elements of the hydrogen mixed gas generation unit 100 other than the vapor heating part 3 are able to be effectively arranged in a space in the casing 1 from the left wall 13 to the front wall 12, so that it is possible to miniaturize the hydrogen mixed gas generation apparatus 10.

As illustrated in FIG. 4, a plurality of outside air introduction ports 161 that also contribute to weight saving of the casing 1 is provided on the bottom wall 16 of the casing 1. Moreover, as illustrated in FIGS. 4 and 5, in the hydrogen mixed gas generation apparatus 10 according to the present embodiment, a fan 9 that forcibly generates ascending air current 600 in the casing 1 is provided so as to face one of the outside air introduction ports 161 that are formed on the bottom wall 16. Herein, the fan 9 is arranged in such a manner that a part thereof overlaps with the vapor heating part 3 in a plan view thereof. That is, the fan 9 is provided so as to face the outside air introduction ports 161 that is provided near the vapor heating part 3 among the plurality of outside air introduction ports 161, and is located in such a manner that a part thereof overlaps with the vapor heating part 3 in a plan view thereof. As such a configuration is provided, outside air rises along a peripheral surface of the vapor heating part 3 so as to improve an air cooling effect.

As illustrated in FIG. 5, by employing the above-mentioned configuration, air drawn by the fan 9 from the outside air introduction ports 161 takes the heat while rising, as the ascending air current 600, along an external surface of the vapor heating part 3, in other words, a surface of the heat insulation material 32.

As illustrated in FIG. 3, a temperature monitoring sensor 102 is provided in an inner part of the casing 1, and the control unit 101 may control driving of the fan 9 in accordance with a detection result of the temperature monitoring sensor 102.

As illustrated in FIG. 5, the back wall 15 is provided with a heat receiving plate 151 that receives radiant heat radiated from the vapor heating part 3 so as to form an air rising path 152 between the heat receiving plate 151 and an inner surface of the back wall 15, through which the ascending air current 600 passes to air-cool the heat receiving plate 151.

In the hydrogen mixed gas generation apparatus 10 according to the present embodiment, the heat receiving plate 151 and the air rising path 152 are also provided on the right wall 14 (see FIG. 4).

As described above, the vapor heating part 3 to be a high temperature is arranged at one of corners of the quadrangular bottom wall 16, and further is arranged closely to two side walls (right wall 14 and back wall 15) so as to actively transfer the heat toward the casing 1. Therefore, the vapor heating part 3 is capable of improving cooling effects in addition to air-cooling by the ascending air current 600.

The ascending air current 600 flowing along an external surface of the vapor heating part 3 and the ascending air current 600 passing through the air rising path 152 smoothly flow from the ventilation holes 132 arranged in an upper part of the side wall to the outside, and thus outside air at room temperature always flows into the casing 1.

As described above, it is possible to largely contribute to health promotion by taking hydrogen mixed gas obtained from the method using the hydrogen mixed gas generation apparatus 10 according to the present embodiment, namely, the hydrogen mixed gas generation method including the first process that includes causing the raw water 500 to flow into the heating pipe 31 and heating the flowing raw water 500 to generate water vapor, further heating the generated water vapor to between 500° C. to 800° C., and causing the heated water vapor to be in contact with the reduction acceleration member 4 that is heated along with the raw water 500 to reduce the water vapor and generate hydrogen gas; and the second process that includes mixing the hydrogen gas generated in the first process with secondary air taken into the system for cooling down to obtain hydrogen mixed gas whose concentration of hydrogen gas is diluted to between 500 ppm to 20000 ppm (0.05 Vol % to 2.0 Vol %).

For example, as illustrated in Table 1, it is found that a great support is gotten regarding health improvement from subjects that take hydrogen mixed gas obtained from the method according to the present embodiment. Table 1 is a summary of survey results for "presence" or "absence" of effects, as result of taking hydrogen mixed gas, which is executed on a plurality of subjects suffering from symptoms such as "malignant tumor", "allergies", and "others".

As illustrated in Table 1, particularly, 12 subjects among 20 subjects suffering from a malignant tumor replied that there presented sufficient effects. Seven subjects replied that there presented effects, and only one subject replied that there presented no effects. Similarly, it was found that replies of subjects suffering from symptoms such as "allergies" and "others" were generally good.

TABLE 1

| Number of Subjects | Symptom | Effects | | |
|---|---|---|---|---|
| | | Present: Sufficient Effects | Present: Effects | Absent: No Effects |
| 20 | Malignant Tumor | 12 | 7 | 1 |
| 10 | Allergies | 4 | 6 | 0 |
| 20 | Others | 11 | 9 | 0 |

Figure 9:
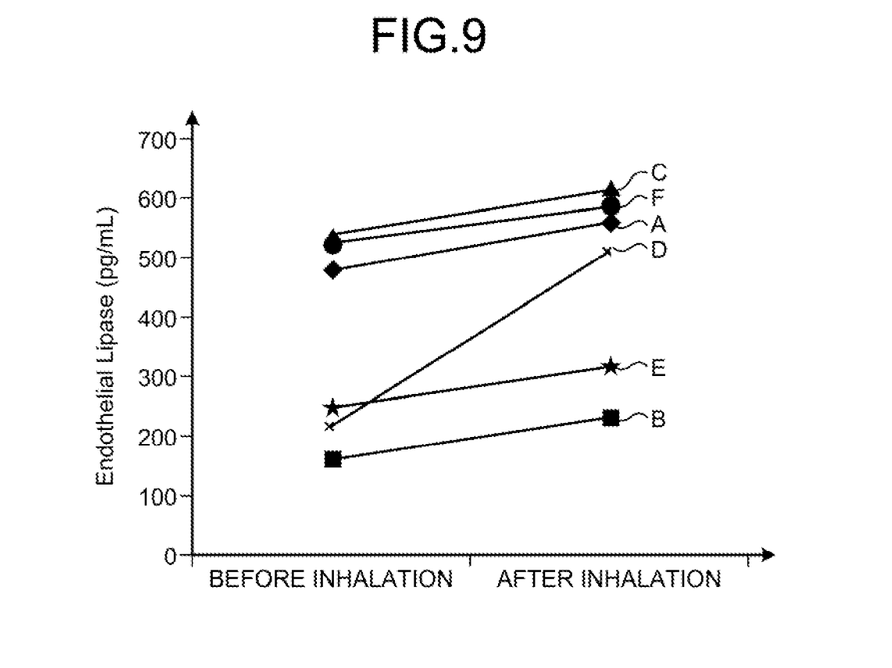
FIG. 9 is a diagram illustrating a fact that there is accelerated production of Endothelial Lipase (EL) in serum after inhalation of hydrogen mixed gas according to the embodiment.

FIG. 9 is a diagram illustrating a fact that there is accelerated production of vascular Endothelial Lipase (EL) in serum after inhalation of hydrogen mixed gas. The vascular Endothelial Lipase (EL) is protein that constantly appears in vascular endothelial cells. When the above-mentioned EL is increased too much, it reduces High-Density Lipoprotein (HDL) that is, i.e. good cholesterol, thereby leading to a state that is not appropriate for a body. However, when the increase is within an appropriate, in other words, physiological range, the increase becomes a good incentive for blood vessels, and there is desired a function for changing blood vessels into a supple state.

As illustrated in FIG. 9, all of the concentrations of vascular endothelial lipase (hereinafter, may be referred to as "EL") in serum rose, which were 90 minutes after subjects A to F that were healthy adults inhaled hydrogen gas. This is recognized as a statistically significant accelerative action.

The increase in EL after inhalation of hydrogen mixed gas was within a physiologically appropriate range. Therefore, a production accelerative action of EL caused by inhalation of hydrogen gas was able to be referred to as a physiological activity of a vascular endothelial cell, and thus the production accelerative action was considered to be a trigger action for activating a physiological function of vascular endothelial cells.

Incidentally, it is considered that the above-mentioned trigger action is effective in the subsequent production acceleration in a nitrate ion ($NO_3^-$) that is an oxidized degradation product of a nitrogen monoxide, an inhibitory action of Angiotensin I-Converting Enzyme (ACE: Angiotensin-Converting Enzyme), and a series of cascade actions that affect an accelerative action of a flow amount of peripheral blood.

Figure 10:
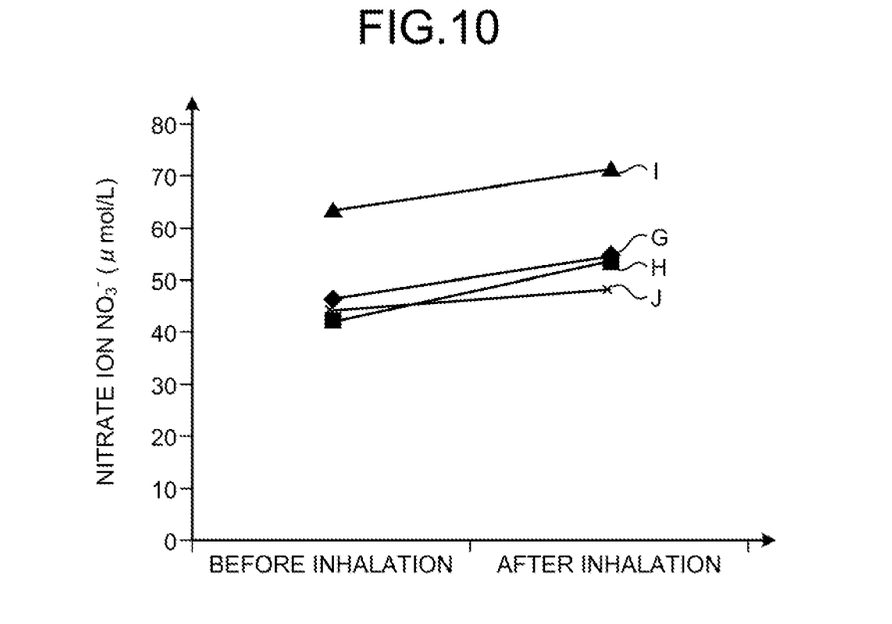
FIG. 10 is a diagram illustrating a fact that there is accelerated production of nitrate ion in serum after inhalation of hydrogen mixed gas according to the embodiment.
Figure 11:
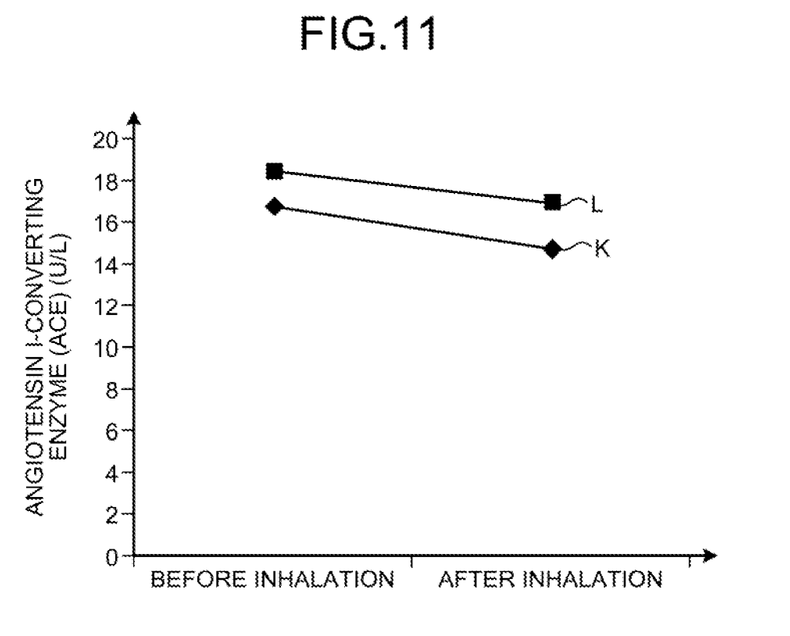
FIG. 11 is a diagram illustrating a fact that there is inhibited angiotensin I-converting enzyme after inhalation of hydrogen mixed gas according to the embodiment.

FIG. 10 is a diagram illustrating a fact that there is accelerated production of nitrate ion in serum after inhalation of hydrogen mixed gas, and FIG. 11 is a diagram illustrating a fact that there is inhibited angiotensin I-converting enzyme after inhalation of hydrogen gas.

As illustrated in FIG. 10, all of the concentrations of nitrate ion ($NO_3$) in serum rose, which were 90 minutes after subjects G to J inhaled hydrogen mixed gas. The result was recognized as a statistically-significant accelerative action.

The induction of nitrate ion in blood means production of Nitric Oxide Synthase (NOS) in a living body. Therefore, the result is considered to finally suggest a smooth muscle relaxant action, a vasodilatory action, and actions for reducing risk of the onset of arteriosclerosis and acute myocardial infarction.

When focusing on angiotensin I-converting enzyme (ACE), as illustrated in FIG. 11, a tendency of inhibitory action was seen in ACE in serum 90 minutes after inhalation of hydrogen gas of subjects K and L.

Angiotensin I-converting enzyme (ACE) is an enzyme that affects adjustment for pressure of blood that is produced by vascular endothelial cells in lungs. The above-mentioned ACE is distributed widely through the whole body, and is present in great quantity particularly in lungs. ACE converts Angiotensin I that is an inactive substance into Angiotensin II that is an active substance, and further inactivates bradykinin that is a kind of biologically active substance having a hypotensive action.

The tendency in which an ACE activity is inhibited within a physiological range after inhalation of hydrogen gas is considered to indirectly suggest, similarly to a medicine that inhibits ACE, a vasodilatory action and a hypotensive action of peripheral blood vessels caused by increase in nitrogen monoxide (NO). It has been reported that an inhibitory action of ACE activity contributes to a hypotensive action of efferent arterioles in kidneys (kidney protecting action directly caused by reduction in intra-glomerular pressure) and an improving action of insulin sensitivity.

Moreover, it has been further reported that inhibition of ACE activity contributes to a pneumonia preventing action (reduction in incidence rate of pneumonia) of an aged person. In other words, it is said that pneumonia of an aged person relates to dysphagia due to reduction in a substance P (kind of neuropeptide stored in ends of C fibers of sensory nerves), which is mainly according to reduction in production of dopamine in cerebral basal ganglia. Namely, inflow of saliva into a lung during nighttime is considered to be a cause of onset of pneumonia.

On the other hand, an ACE-activity inhibiting action after inhalation of hydrogen gas indicates possibility that the action inhibits degradation of a substance P so as to improve reduced swallowing function, so that it is possible to expect an action for preventing silent aspiration during nighttime leading to an action for preventing onset of pneumonia.

Figure 12:
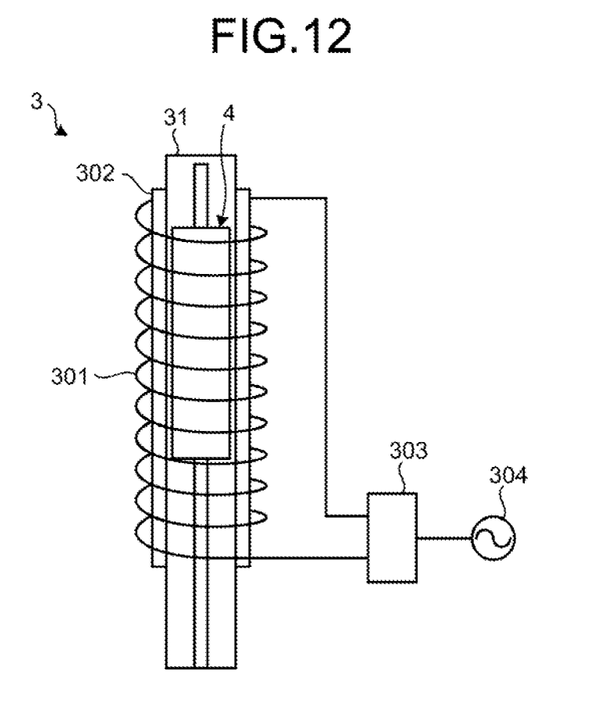
FIG. 12 a schematic explanatory diagram illustrating one example of a heating part in a hydrogen mixed gas generation apparatus according to another embodiment.

Next, a hydrogen mixed gas generation method according to another embodiment will be explained. FIG. 12 is a schematic explanatory diagram illustrating one example of a heating part in a hydrogen mixed gas generation apparatus according to another embodiment.

In the above-mentioned example, the vapor heating part 3 included in the hydrogen mixed gas generation apparatus has a configuration including, as a heating device, the coil heater 7 that is wound around a periphery of the heating pipe 31. However, the heating device is not limited to the coil heater 7. For example, as illustrated in FIG. 12, the heating device may be an electromagnetic induction heating device, namely, a heating device with the use of Induction Heating (IH).

In other words, as illustrated in FIG. 12, in a heating device of the vapor heating part 3 included in the hydrogen mixed gas generation apparatus according to another embodiment, an IH coil 301 is arranged around the heating pipe 31 in which there is housed the reduction acceleration member 4 including the iron rod member 412 formed of steel material. The IH coil 301 is connected to a commercial power source 304 via an IH controlling circuit 303. The IH controlling circuit 303 is provided with, for example, an inverter circuit, a control circuit that controls the inverter circuit, and the like.

Thus, when a high-frequency wave current flows into the IH coil 301, an eddy current flows into the iron rod member 412 by electromagnetic induction so as to heat the iron rod member 412.

In the above-mentioned other embodiment, the IH coil 301 is arranged around the heating pipe 31 via a wound base material 302 arranged around the heating pipe 31; however, arrangement of the IH coil 301 and the like may be preferably set.

As a metal for generating an eddy current, the reduction acceleration member 4 including the iron rod member 412 is used; however, a metal body may be separately arranged.

Incidentally, in the above-mentioned embodiments, the gas intake part 55 including a pinhole is formed in the cap body 400 attached to the heating pipe 31, and outside air is taken from the gas intake part 55 as secondary air so as to dilute hydrogen mixed gas at a high temperature in which hydrogen gas and superheated vapor are mixed with each other.

However, an object to be taken from the gas intake part 55 may be, instead of air, gas (hereinafter, may be referred to as "diluent gas") not including $O_2$ (oxygen). For example, nitrogen gas and the like may be preferably employed as the diluent gas. In this case, a tank (not illustrated) filled with the diluent gas may be connected with the gas intake part 55 in communication with each other.

The diluent gas does not contain $O_2$ (oxygen), and thus hydrogen atoms containing hydrogen radicals considered to be contained in vapor mixed gas do not react with oxygen atoms and the like. Therefore, it is possible to reduce, as much as possible, effects on virtue of hydrogen mixed gas that is extremely good for health maintenance of a human body.

As described above, when diluent gas is taken into vapor mixed gas containing hydrogen gas, a concentration of hydrogen mixed gas is diluted to within a range between 1000 ppm to 3000 ppm, and is further cooled down to a temperature appropriate for intake into a human body. Note that in this case, a diameter of the gas intake part 55 and the like are also set in accordance with a required amount of the diluent gas.

For example, when diluent gas and vapor mixed gas are mixed with each other and to be transferred to the gas inhalation tube 30 by operation of the gas supply fan 81, there presents no need for providing the gas intake part 55 having the above-mentioned configuration.

According to the above-mentioned embodiments, the following hydrogen mixed gas generation methods are realized.

(1) A hydrogen mixed gas generation method using a device that includes a heating pipe housing therein the reduction acceleration member 4 and a heating part including a heating device that heats the heating pipe, the method including: a first process including: causing the raw water 500 to flow into the heating pipe 31 and heating the flowing raw water 500 to generate water vapor; heating the generated water vapor to between 500° C. to 800° C.; causing the heated water vapor to be in contact with the reduction acceleration member 4 that is heated along with the raw water 500 to reduce the water vapor and generate hydrogen gas; and a second process including: a second process that includes mixing the hydrogen gas generated in the first process with secondary air taken into a system for cooling down to obtain hydrogen mixed gas whose concentration of hydrogen gas is diluted to between 500 ppm to 20000 ppm. It is preferable that a temperature range in the heating of the generated water vapor is between 650° C. to 750° C.

According to the above-mentioned method, it is possible to efficiently obtain hydrogen mixed gas that is extremely good for health maintenance of a human body.

(2) In a hydrogen mixed gas generation method according to the above-mentioned (1), the vapor heating part 3 includes the coil heater 7 that is wound around the heating pipe 31.

(3) In a hydrogen mixed gas generation method according to the above-mentioned (1), the vapor heating part 3 includes an electromagnetic induction heating device.

When an electromagnetic induction heating device is employed for the vapor heating part 3, a whole device is able to be miniaturized.

(4) In a hydrogen mixed gas generation method according to any one of the above-mentioned (1) to (3), a concentration of the hydrogen gas in the hydrogen mixed gas obtained in the second process is between 1000 ppm to 3000 ppm.

According to the above-mentioned method, it is possible to more reliably obtain hydrogen mixed gas that is extremely good for health maintenance of a human body.

According to the above-mentioned method, a hydrogen concentration of the hydrogen gas whose concentration is relatively high, which is obtained in the former step, is able to be easily diluted down to a predetermined range for exerting effects on a human body.

(5) In a hydrogen mixed gas generation method according to any one of the above-mentioned (1) to (4), the reduction acceleration member 4 includes the holding member 411 that is formed of stainless and includes the cylindrical part 43 where the rod bodies 41a and 41b respectively extend from both ends of the cylindrical part 43; and the plurality of iron rod members 412 that is formed of the steel materials 42 and is housed in the cylindrical part 43 in a bundled state.

According to the above-mentioned method, by using an activated reduction acceleration member, water vapor at a high temperature is able to be effectively reduced to obtain hydrogen gas, and further the reduction acceleration member is able to be formed in a cartridge, so that maintenance work such as replacement is easy.

(6) In a hydrogen mixed gas generation method according to the above-mentioned (5), lengths of the rod bodies 41a and 41b respectively extending from the cylindrical part 43 in the holding member 411 are set such that the cylindrical part 43 is not in contact with the raw water 500.

(7) In a hydrogen mixed gas generation method according to any one of the above-mentioned (1) to (6), hydrogen mixed gas is obtained, whose concentration is diluted to 500 ppm to 20000 ppm, by mixing hydrogen gas generated in the first process and diluent gas not containing oxygen with each other.

In the hydrogen mixed gas generation apparatus 10 according to the present embodiment, the rectangular-box-shaped casing 1 effectively houses therein the hydrogen mixed gas generation unit 100 to obtain a compact structure. Additionally, the hydrogen mixed gas generation apparatus 10 according to the present embodiment houses therein the vapor heating part 3 that becomes a high temperature; however, arrangement thereof is worked out to realize a structure capable of performing effective air cooling, so that it is possible to prevent the casing 1 from being heated to a high temperature. Furthermore, the reduction acceleration member 4 to be a reduction acceleration member is housed in the heating pipe 31 of the vapor heating part 3, dilution is performed by using secondary air taken from a pinhole of 1.0 mm to 2.0 mm, so that it is possible to stably generate hydrogen mixed gas whose concentration is 1000 ppm to 3000 ppm (0.1 Vol % to 0.3 Vol %).

Not limited to the above-mentioned embodiments, even when a diameter of a pinhole is set to less than 5 mm and further a hydrogen concentration of finally obtained hydrogen mixed gas is 500 ppm to 20000 ppm, it is possible to obtain hydrogen mixed gas that is extremely good for health maintenance of a human body.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

The invention claimed is:

1. A hydrogen mixed gas generation method using a device that includes a heating pipe housing therein a reduction acceleration member and a heating part including a heating device that heats the heating pipe, the method comprising:
   a first process including:
      causing raw water to flow into the heating pipe and heating the flowing raw water to generate water vapor;
      heating the generated water vapor to between 500° C. to 800° C.;
      causing the heated water vapor to be in contact with the reduction acceleration member that is heated along with the raw water to reduce the water vapor and generate hydrogen gas; and
   a second process including:
      diluting the hydrogen gas generated in the first process to obtain hydrogen mixed gas whose concentration of hydrogen gas is between 500 ppm to 20000 ppm, wherein
   the reduction acceleration member includes:
      a first metal member that is formed of stainless and includes a cylindrical part where rod bodies respectively extend from both ends of the cylindrical part; and
      a plurality of second metal members that is formed of a steel material and is housed in the cylindrical part in a bundled state.

2. The hydrogen mixed gas generation method according to claim 1, wherein
   lengths of the rod bodies respectively extending from the cylindrical part in the first metal member are set such that the cylindrical part is not in contact with the raw water.

3. The hydrogen mixed gas generation method according to claim 1, wherein
   the heating part includes a coil heater that is wound around the heating pipe.

4. The hydrogen mixed gas generation method according to claim 1, wherein
   a concentration of the hydrogen gas in the hydrogen mixed gas obtained in the second process is between 1000 ppm to 3000 ppm.

5. The hydrogen mixed gas generation method according to claim 1, wherein
   the second process includes:
      mixing the hydrogen gas generated in the first process with secondary air taken into a system for cooling down to obtain hydrogen mixed gas whose concentration of hydrogen gas is diluted to between 500 ppm to 20000 ppm, and
   the secondary air is taken from a pinhole whose diameter is less than 5 mm.

6. The hydrogen mixed gas generation method according to claim 1, wherein the heating part includes an electromagnetic induction heating device.

* * * * *